(12) United States Patent
Arcand

(10) Patent No.: US 6,368,353 B1
(45) Date of Patent: Apr. 9, 2002

(54) SHOULDER PROSTHESIS APPARATUS AND METHODS

(76) Inventor: Michel A. Arcand, 3613 Bridgeport Rd., Norman, OK (US) 73072

( * ) Notice: Subject to any disclaimer, the term of this patent is extended or adjusted under 35 U.S.C. 154(b) by 0 days.

(21) Appl. No.: 09/511,356

(22) Filed: Feb. 23, 2000

Related U.S. Application Data (60) Provisional application No. 60/121,475, filed on Feb. 24, 1999.

(51) Int. Cl.[7] .................................................. A61F 2/40
(52) U.S. Cl. ................... 623/19.13; 623/19.11; 623/19.12; 623/19.14
(58) Field of Search ................ 623/19.11, 19.12, 623/19.13, 19.14

(56) References Cited

U.S. PATENT DOCUMENTS

| | | | | |
|---|---|---|---|---|
| 4,123,806 A | * | 11/1978 | Amstutz et al. | 623/22.39 |
| 4,550,450 A | | 11/1985 | Kinnett | 623/18 |
| 4,700,702 A | * | 10/1987 | Nilsson | 606/177 |
| 4,709,699 A | * | 12/1987 | Michael et al. | 606/177 |
| 4,893,619 A | * | 1/1990 | Dale et al. | 606/82 |
| 4,964,865 A | * | 10/1990 | Burkhead et al. | 623/19.11 |
| 5,314,479 A | * | 5/1994 | Rockwood, Jr. et al. | 623/19.14 |
| 5,702,486 A | * | 12/1997 | Craig et al. | 623/19.14 |
| 5,800,551 A | * | 9/1998 | Williamson et al. | 623/19.11 |

* cited by examiner

*Primary Examiner*—David J. Isabella
(74) *Attorney, Agent, or Firm*—Greenberg Traurig; Richard E. Kurtz, II (57) ABSTRACT

A total shoulder replacement arthroplasty system which encompasses replacement of the humeral head with a modular artificial humeral head. The artificial humeral head is attached to an implant, which is designed to fit in the metaphysis without protruding into the diaphysis, thus obviating the need to ream the diaphysis. In addition, the implant is designed to allow bone in-growth into the implant, thus avoiding the use of cement to affix the implant. A device for resecting the humeral head to facilitate easy implantation of the prosthetic is also disclosed, as is an operative technique used to implant the prosthetic.

7 Claims, 8 Drawing Sheets

SHOULDER PROSTHESIS APPARATUS AND METHODS

This application claims the benefit of U.S. Provisional Patent Application Ser. No. 60/121475 filed Feb. 24, 1999, the entire disclosure of which is incorporated herein by reference.

This application includes material which is subject to copyright protection. The copyright owner has no objection to the facsimile reproduction by anyone of the patent disclosure, as it appears in the Patent and Trademark Office files or records, but otherwise reserves all copyright rights whatsoever.

BACKGROUND OF THE INVENTION

1. Field of the Invention

The invention relates in general to human joint replacement through the use of a prosthesis, and in particular to total shoulder prosthetics.

2. Related Art

The shoulder joint is the largest joint in the human upper torso, and functions as the fulcrum for all upper torso activities. Like knees and hips, the shoulder is a heavily used joint, often called upon to support or transmit high forces. However, unlike knees and hips, shoulders also have a wide range of motion. The shoulder's unique combination of features comes at the cost of stability. A shoulder may become problematic due to several disorders and conditions. These disorders can lead to abnormal wear similar to those suffered by the weight bearing joints of the lower extremity. Thus, replacement of portions of the shoulder that contact each other, typically the epiphysis of the humerus, or humeral head, and the epiphysis of the scapula, or glenoid, is a fairly common procedure.

Given the frequency with which shoulder arthroplasty, the replacement of the humeral head and glenoid, is performed, surprisingly little research has been performed to design shoulder-specific prosthetics. In fact, due to similarities of the hip and shoulder joints, typical shoulder prosthetics have been little more than slightly redesigned hip prosthetics. However, as previously mentioned, human hips do not have the same range of motion as human shoulders, and the anatomical design of the femur, the primary hip bone, is different from the humerus, the primary bone of the shoulder. These differences lead to significant deficiencies in typical shoulder prosthesis designs.

Traditional shoulder replacement involves removal of the head of the humerus, extensive reaming of the diaphysis of the humerus, and insertion of a long (typically ten or more centimeters) metallic stem into the diaphysis to increase overall prosthetic leverage and stability. The inserted stem is then cemented into place, effectively immobilizing the rod and strengthening the connection between the rod and the humerus. The top of the inserted rod may be designed to accept an artificial humeral head, and the mounting of such a head completes the reconstruction.

Although long prosthetic stems increase leverage and stability, long prosthetic stems also cause stress shielding of the proximal humeral metaphysis. A long stem causes stress to bypass the metaphysis, which results in bone loss and associated loss of function. An example of this is loss of the greater tuberosity with the resultant loss of rotator cuff function.

This loss of proximal bone also creates difficulties with revision procedures. Cement in the metaphysis and the diaphysis of the humerus can be difficult to remove during revision of prosthetic stems. Removal of cement, combined with thin and atrophic bone that results from stress shielding, makes prosthesis revision even more difficult.

In addition to stem insertion, other techniques exist for the replacement of some or all of the shoulder. For example, U.S. Pat. No. 4,550,450 ("the '450 patent") teaches replacement of a portion of the humeral head with high density plastic, ceramic, or metallic surfaces, without the use of a rod in the diaphysis. However, the '450 patent uses a small trapezoidal keel which is inserted into the metaphysis. To accommodate the keel and properly anchor it in place, the metaphysis must be reamed and the keel must be cemented into place.

While the '450 patent allows for humeral head replacement without the insertion of a long rod into the diaphysis, the '450 patent has several deficiencies. For example, the '450 patent does not allow the use of modular components. Without modularity, a surgeon is limited in the choice of humeral heads and stem sizes. The '450 patent also has a centered head, rather than an offset head. A centered head does not cover the metaphysis as well as an offset head. In addition, the '450 patent requires the use of cement to hold the stem in place. Introducing cement into the metaphysis can result in significant bone loss when revising this type of prosthesis, due to cement forced into bone pores during implantation.

OBJECTS AND SUMMARY OF THE INVENTION

It is therefore an object of the invention to provide an improved shoulder prosthesis.

Another object of the invention to allow the use of a modular prosthetic humeral head in conjunction with such a prosthesis.

It is a further object of the invention to allow implantation of support structures for such a humeral head while reducing or eliminating the need for cement or other bonding materials.

Yet another object of the invention is to provide adequate prosthetic strength without reaming or insertion of rods or other devices into the diaphysis.

A further object of the invention to provide an increased range of motion by more naturally matching prosthetic and natural humerus and glenoid shapes.

In a preferred embodiment, the invention provides these and other objects as a result of a reconceptualization of total shoulder arthroplasty. While known total shoulder prostheses have been designed using principles developed for prosthetic hips, the present invention has been designed specifically for shoulder arthroplasty. In addition, the present invention also allows for fracture repair using techniques and apparatuses similar to those used in an arthroplasty. The preferred embodiment includes a new humeral head replacement for osteoarthritis and other degenerative disorders, a new total shoulder prosthesis, a new fracture component and revision stem, and a new method of assembling, inserting, and attaching the prosthesis.

The humeral head replacement of the preferred embodiment includes an implant that allows the attachment and removal of modular artificial humeral heads. The use of modular heads allows customization of the prosthesis for each patient. Such an implant also allows head replacement in the event a previously installed artificial head wears out, becomes deformed, or otherwise requires replacement.

In addition, the preferred implantation method allows for less bone loss when and if the prosthesis needs to be revised. To help reduce bone loss during revisions, the implant is preferably designed to obviate the need for cement when installed. Use of a non-cemented fixation technique is desirable because cement can reduce patient life expectancy due to the toxicity of some cements.

In a preferred embodiment, the implant may be fixated by a press fit of the prosthesis into the humeral metaphysis. Autogenous bone graft may be used to improve the fit and encourage in-growth into the porous coat of the prosthesis. In an alternative embodiment, a mixture of autogenous graft, plaster of Paris and bone morphogenic protein or another osteogenic substance may be used to increase in-growth into the implant.

Further aspects of the invention include instruments that allow implantation of the new device. Instrumentation is kept simple in an attempt to keep the number of instruments at a reasonable level.

In a further aspect of the invention, the present invention may accept modular heads that support different head neck angles, as well as offset heads. These two design features help maximize the amount of contact between a porous coating on the prosthesis and the humeral metaphysis. Offset heads may include guides which are marked to allow accurate reproduction to be made on the implant.

The porous coating of the implant and head encourages metaphyseal bone to grow around and fuse with the prosthesis. Bone in-growth into the porous coating fuses the prosthesis with the surrounding bone, fixing and stabilizing it to the bone without cement. In addition, bone and prosthesis fusion may constitute a barrier to the migration of polyethylene particles into the humeral metaphysis and shaft. This may prevent these particles from causing osteolysis of the bone.

The foregoing and other objects, features, and advantages of the invention will be apparent from the following more particular description of preferred embodiments as illustrated in the accompanying drawings, in which reference characters refer to the same parts throughout the various views. The drawings are not necessarily to scale, emphasis instead being placed upon illustrating principles of the invention.

DETAILED DESCRIPTION

The present invention comprises a new and unique humeral head replacement for osteoarthritis and other shoulder ailments, a new total shoulder prosthesis, and a new method for affixing the prosthesis to the humerus. One aspect of the present invention is a humeral implant that allows for less bone loss if revision of the prosthesis is necessary. In addition, the humeral implant facilitates alignment of an artificial modular humeral head by insertion of an anchor point in the humeral metaphysis.

In addition to facilitating improved alignment, the humeral implant is designed to preserve as much bone stock as possible by allowing the implant to be press fit in place, rather than cemented. A non-cemented approach is desirable for several reasons. First, a non-cemented approach reduces the incidence of particulate disease because polymethylmethacrylate, a common cement, is not used. In addition, when a traditional implant is revised, cement surrounding the implant must be removed prior to the installation of a new implant. Removal of old cement typically results in the loss of additional bone.

A press-fit alone is not typically stable enough to provide proper implant support initially, therefore, in a preferred embodiment, the humeral implant is made of titanium which has been textured to allow bone in-growth. Bone in-growth may further support and stabilize the implant. In addition, the proximal fixation of the prosthesis allows the metaphyseal bone distally to bear stress and decrease its likelihood of atrophying.

In addition to employing an a press fit fixation technique, the present invention also includes a reassessment of humeral head and implant design. Unlike the head of the femur, which sits atop a long anatomical neck, the humeral head rests atop a short neck, effectively placing the humeral head directly on the metaphysis. Because the humeral head rests on the metaphysis, the metaphyseal bone can grow into the undersurface of the head.

By maximizing contact between an artificial humeral head and the humerus, the implant portion of present invention can be made shorter than prior humeral implants while still providing necessary torsional and impact strength. The present invention provides stability and torque similar to implants which include a diaphyseal component, while requiring only marginally more bone resection than the '450 patent.

Figure 8:
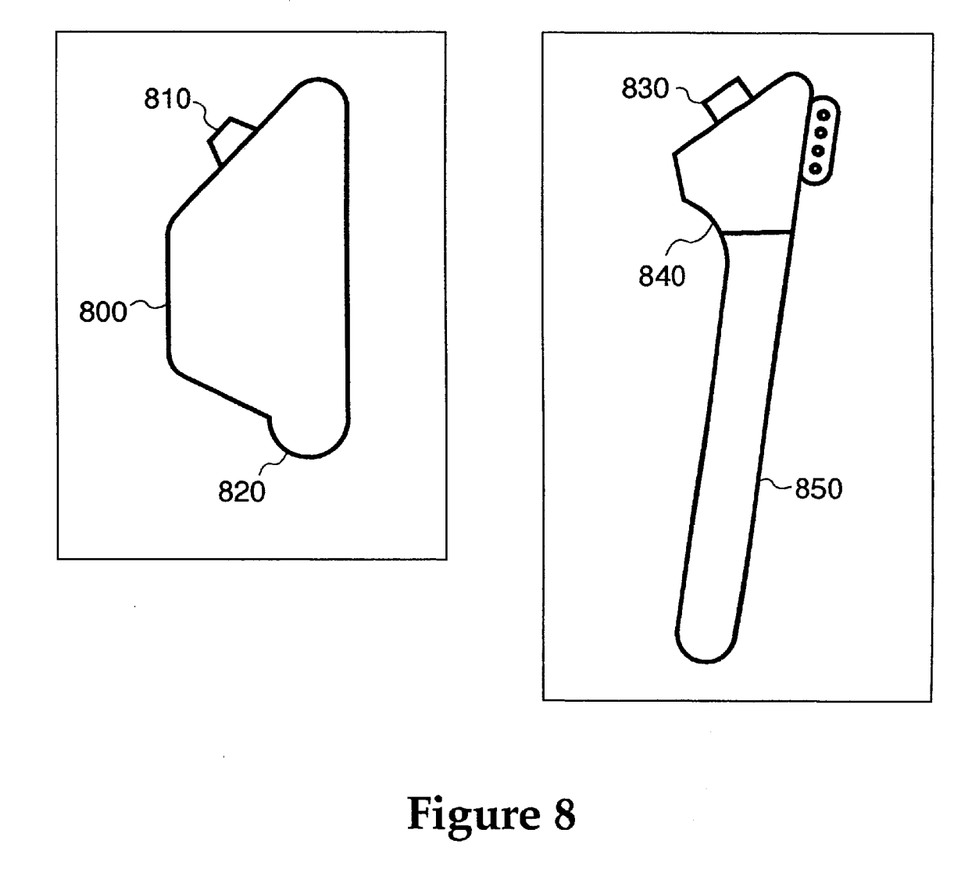
FIG. 8 illustrates the shorter length of the humeral implant of the present invention, as compared to a traditional implant.
Figure 9:
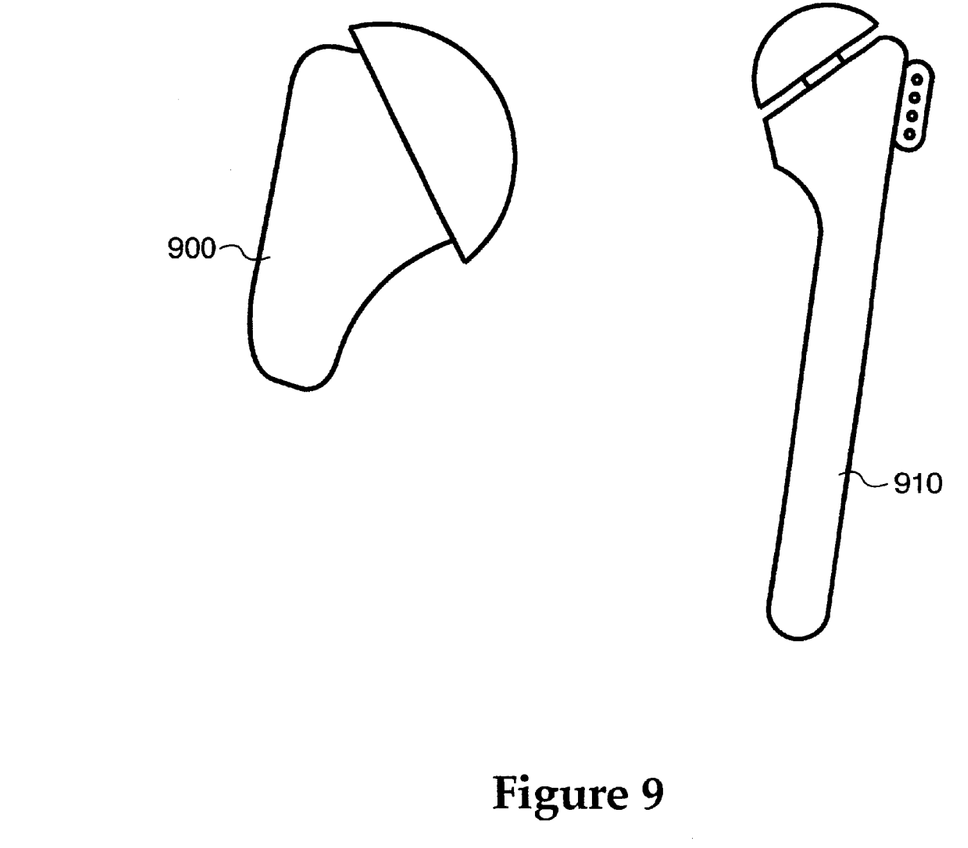
FIG. 9 is a comparison of complete humeral prostheses as described by the prior art and by the present invention.

In addition, the present invention improves prior art by providing a platform to which a modular artificial head may be attached. Comparisons of humeral implants taught by the prior art and implants of the present invention are illustrated by FIGS. 8 and 9. FIG. 8 illustrates the significant difference in length between a stem 820 as used in the present invention and the stem of a traditional implant 850. The body 800 of the present invention is also a different shape from the body 840 used in the prior art. In addition, stem 810 of the present invention may be at a different angle from stem 830 of the present invention. FIG. 9 illustrates the present invention 900 and prior implants 910 with artificial humeral heads attached.

Figure 1:
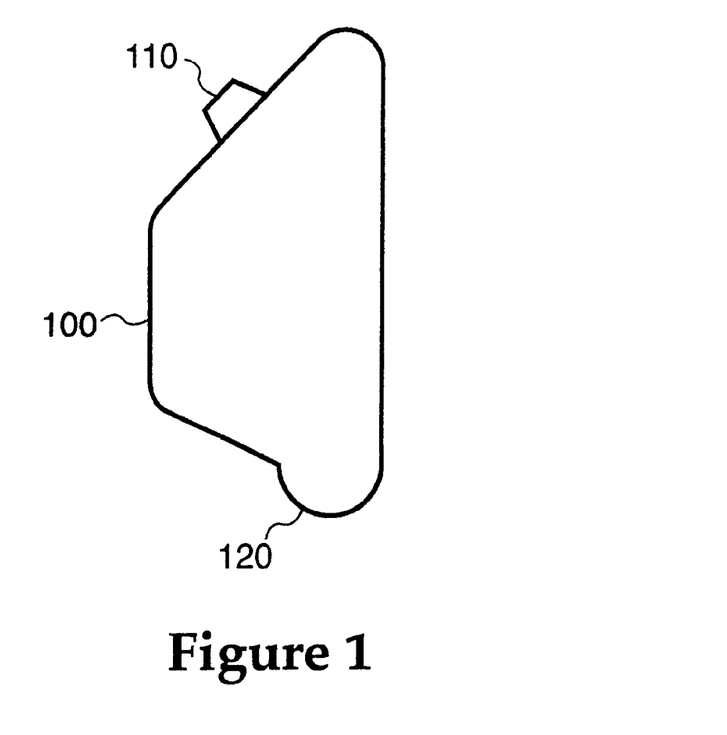
FIG. 1 illustrates a side elevational view of a humeral implant, from which the trapezoidal shape of the implant can be discerned.

As illustrated in FIG. 1, in a presently preferred embodiment, a side view of the modular humeral implant 100 is approximately trapezoidal in shape, although all edges of the present invention are rounded. In addition to the generally trapezoidal shape, the present invention may include a post 110 and a stem 120. Although a stem 120 is included to assist in proper implant alignment, stem 120 typically does not extend into the diaphysis of the humerus.

Figure 2:
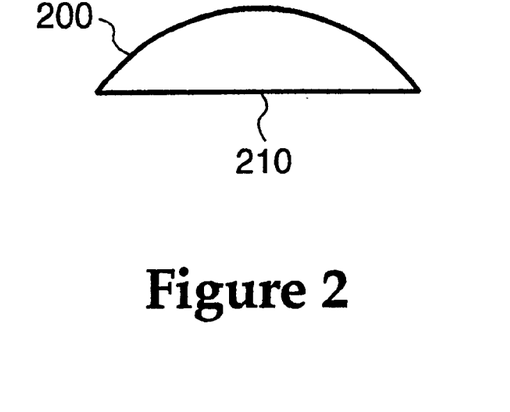
FIG. 2 is a side elevational view of a humeral head, from which the hemispheric shape of the humeral head can be discerned.
Figure 3:
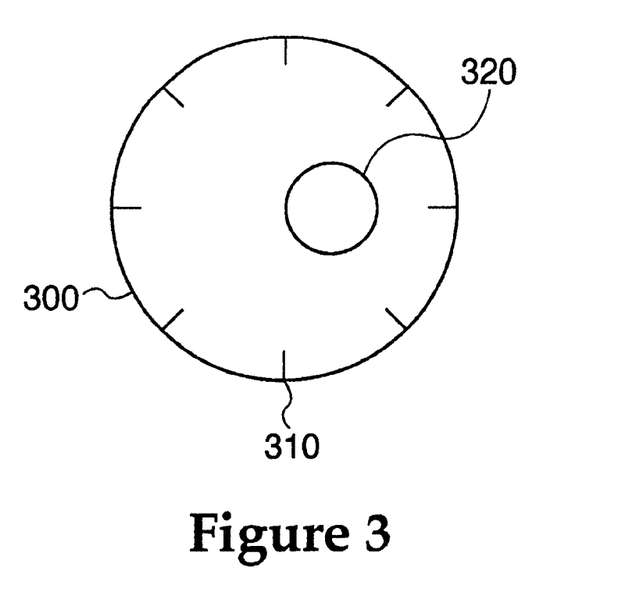
FIG. 3 is a top view of a modular humeral head with an offset mounting hole.
Figure 4:
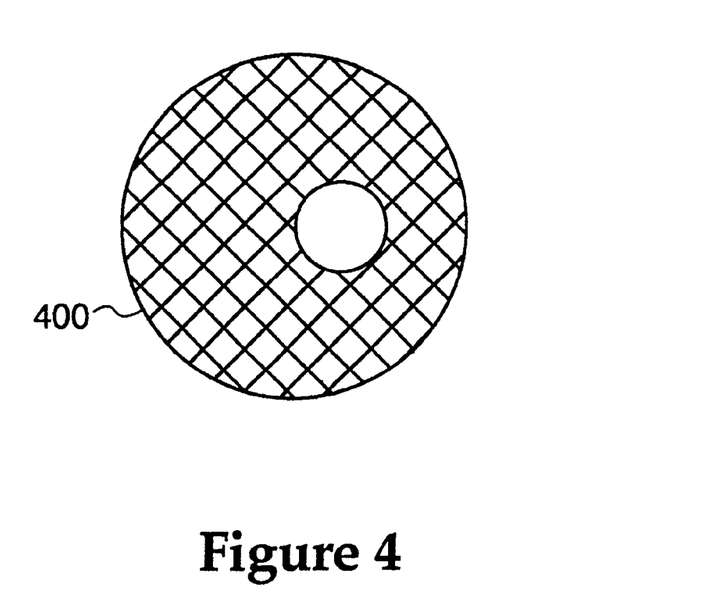
FIG. 4 is an undersurface view of a modular humeral head, from which a porous coating can be discerned.

Post 110 represents a fixture to which a modular humeral head, illustrated in FIGS. 2 through 4, may be attached. In an alternative embodiment, modular humeral implant 100 may have a morse taper, or hole, in the position of post 110, which can allow a head to be attached through the insertion of a post which can allow the head to be fixed to the stem. In an additional alternative embodiment, a stem 120 may extend slightly (typically one to two centimeters) into the diaphysis of the humerus.

Although the implant may be circumferentially covered with a two centimeter area of porous material to encourage bone in-growth, it is contemplated that the distal stem 120 should not be made of porous material. A solid, smooth stem 120 is recommended because bone in-growth in the stem area may make implant removal more difficult. In addition, removal of an implant with bone in-growth at the stem may lead to additional bone loss, therefore a smooth stem is preferred.

Figure 7:
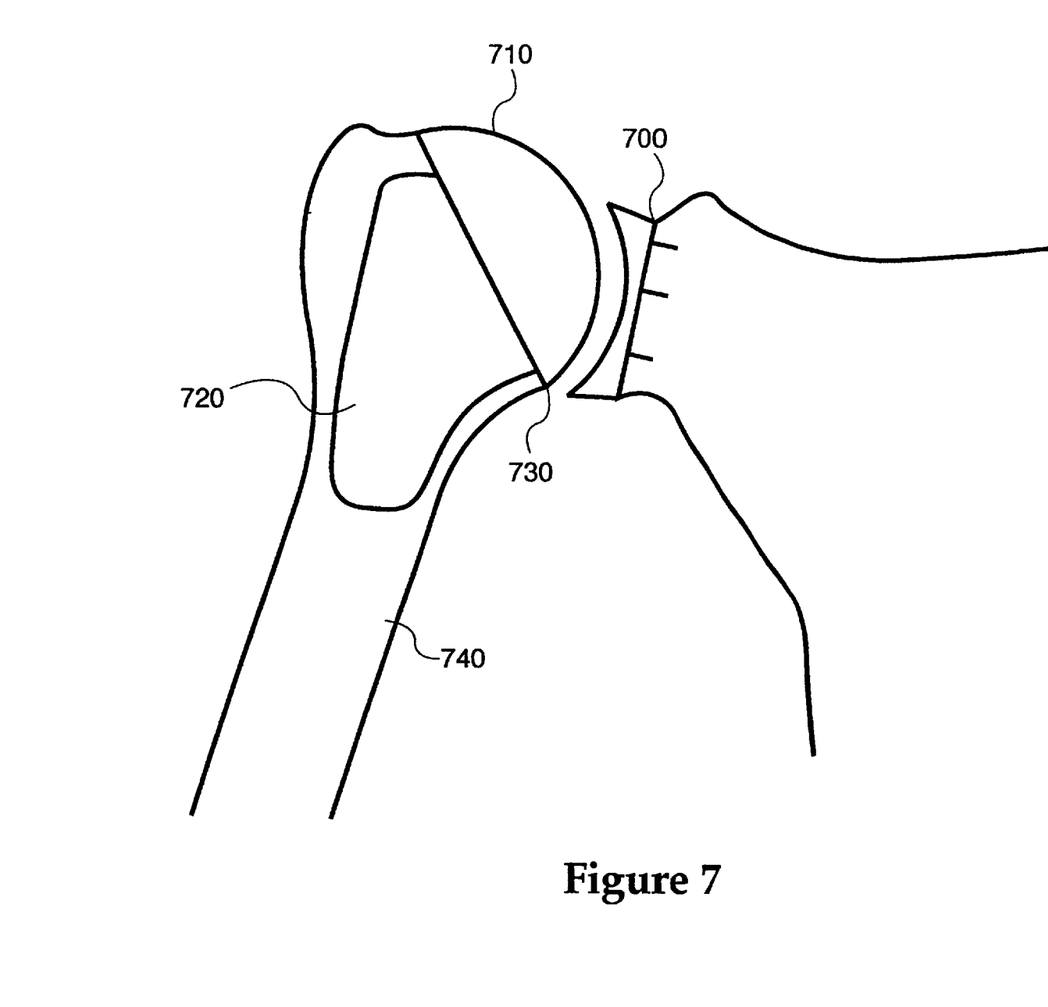
FIG. 7 is an anterior view of the present invention as positioned in the metaphysis with a pegged glenoid component.

In an additional alternative embodiment, a textured collar 730 may be applied overtop of the implant 720, thereby facilitating bone in-growth overtop of the implant and further reinforcing the implant. In this embodiment, a collar may have a porous area on the surface contacting the metaphysis and a smooth area on the side facing the replacement humeral head 710. In such an alternative embodiment, a collar may be inserted between a metaphyseal component and an artificial humeral head, as illustrated in FIG. 7.

As illustrated in FIGS. 2 through 4, a modular humeral head component 200, with an undersurface 210 covered by a porous in-growth surface, may be used in a further alternative embodiment. The textured undersurface is illustrated in more detail in FIG. 4. In this embodiment, in-growth occurs on the metaphyseal section of the head, thus alleviating the need for a collar. In addition to the porous area on the metaphyseal section, the modular humeral head component may utilize an offset mounting hole or post 320, thereby allowing better coverage of the humeral metaphysis.

The modular humeral head approach favored by the present invention allows a surgeon to select appropriate head size, head neck angle, offset, and other characteristics, thus customizing the prosthesis for each patient. Accepting a variety of artificial humeral heads also helps maximize contact between the porous prosthesis coating and the humeral metaphysis.

In a preferred embodiment, a modular humeral head composed of cobalt chrome or other high tensile strength material should be used. Cobalt chrome is preferred over titanium because titanium is often too soft to be used in this application. Although cobalt chrome is preferred, artificial heads composed of other materials, such as ceramics, are also contemplated.

Figure 5:
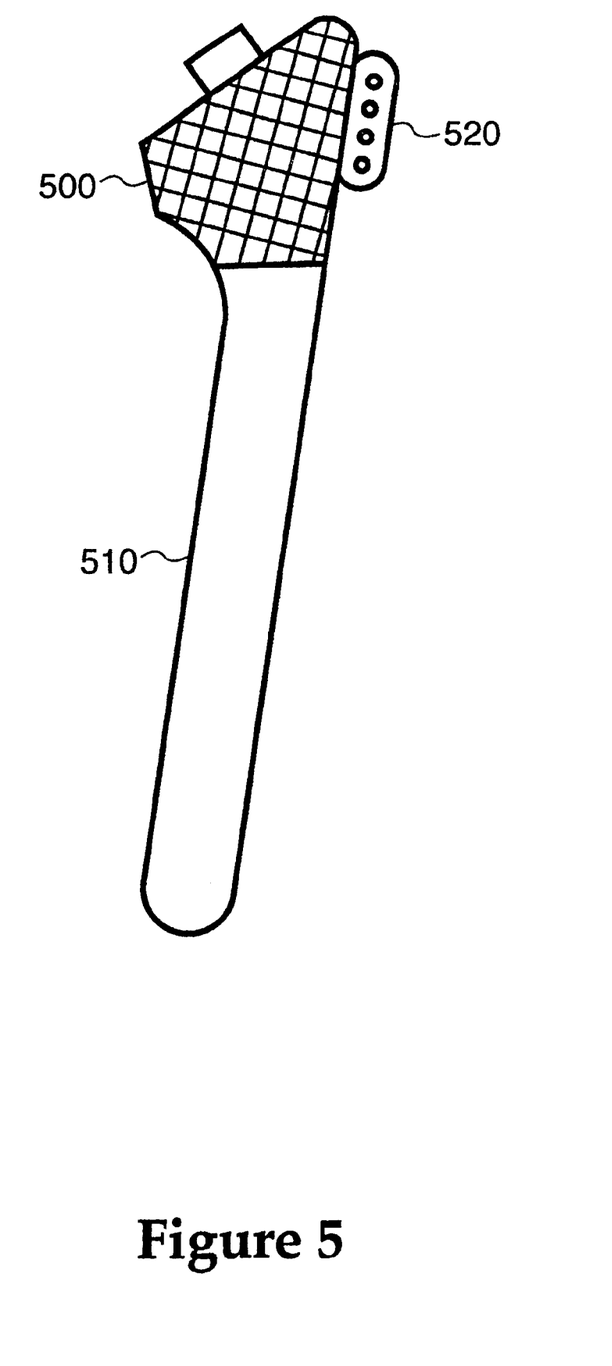
FIG. 5 illustrates a fracture and revision stem aspect of the present invention.

In an additional alternative embodiment, illustrated in FIG. 5, the present invention may be used in a fracture system. A fracture system allows a surgeon to replace or bypass crushed portions of the epiphysis, metaphysis, and diaphysis through the addition of a prosthesis. This is preferred due to the extent of bone loss in fractures. In the event a fracture system is necessary, reamers may be used to center the prosthesis on the humeral shaft. In a preferred embodiment, a fracture system of the present invention may be similar to systems in use. However, unlike current fracture systems, a fracture system embodiment of the present invention includes a region for bone in-growth 500 in the metaphyseal and undersurface of the epiphyseal portions of the implant.

The fracture and revision system is built using the previously described arthritic implant, to which a diaphyseal stem 510 is molded onto the metaphyseal replacement. A stem should be selected which, when inserted into the diaphysis, supports the prosthesis at the appropriate height. Insertion of the stem into the diaphysis also allows a fracture system to be cemented in place, which may be desirable in the fracture situation because the prosthesis should remain proud for tubercle fixation. As previously described, metaphyseal section of the fracture system includes a porous region to allow in-growth of the fractured tuberosity bone onto the prosthesis.

An artificial humeral head or collar with an in-growth surface may be attached to the fracture stem, as described above in the arthritic component section. An offset head is preferred, as an offset head allows for better coverage of the repaired tuberosities. Extra area for bone in-growth provided by a head or collar may increase the likelihood of tuberosity union. In a preferred embodiment, medial and lateral fins 520 are also provided, thus adding stability when repairing tuberosities onto the metaphyseal portion of the prosthesis.

In addition to replacing the humeral head, the glenoid is also replaced in total shoulder replacements. Artificial glenoid components come in different sizes, and an artificial glenoid which closely matches the size of the natural glenoid should be selected. Matching sizes may allow better artificial glenoid stability.

Figure 6:
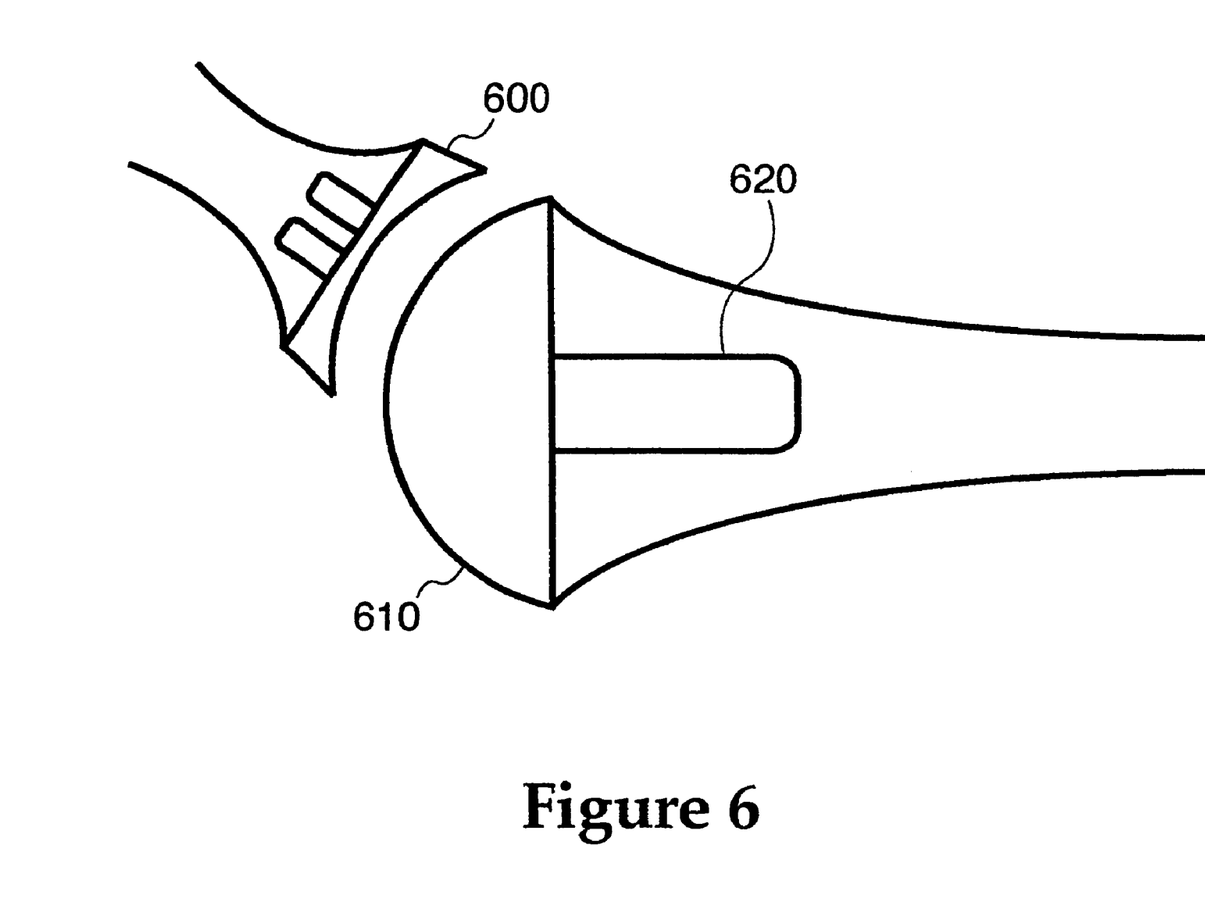
FIG. 6 is an axillary view of the present invention as positioned in the metaphysis with a glenoid component.

In a preferred embodiment illustrated in FIG. 6, an artificial glenoid component 600 should be seven millimeters in thickness and composed entirely of polyethylene. In an alternative embodiment, a metal humeral head 610 articulated on a metal artificial glenoid is contemplated. In a second alternative embodiment, a ceramic head articulated on a polyethylene artificial glenoid is contemplated. A metal-backed artificial glenoid is not presently preferred, but a metal-backed artificial glenoid may be useful in the future, or an artificial glenoid made of new materials may be used.

As illustrated in FIG. 7, the radius of curvature of an artificial glenoid component 700 should closely match the radius of curvature of the humeral head 710. In a preferred embodiment, the curvature of the glenoid 700 should not exactly match the radius of curvature of the humneral head 710 because a more physiologic pattern of motion, in which some translation of the humeral head 710 may occur on the glenoid 700, has been noted using a slight mismatch (approximately two millimeters) in the radii of curvature between the components.

In a presently preferred embodiment, a pegged artificial glenoid, as illustrated in FIGS. 6 and 7, should be used. A pegged artificial glenoid 700 is preferred as pegged artificial glenoids provide improved stability under mechanical testing. In an alternative embodiment, a keeled glenoid may be used. Keeled glenoids are not preferred, as they require the reaming of a large hole in the center of the natural glenoid.

Figure 10:
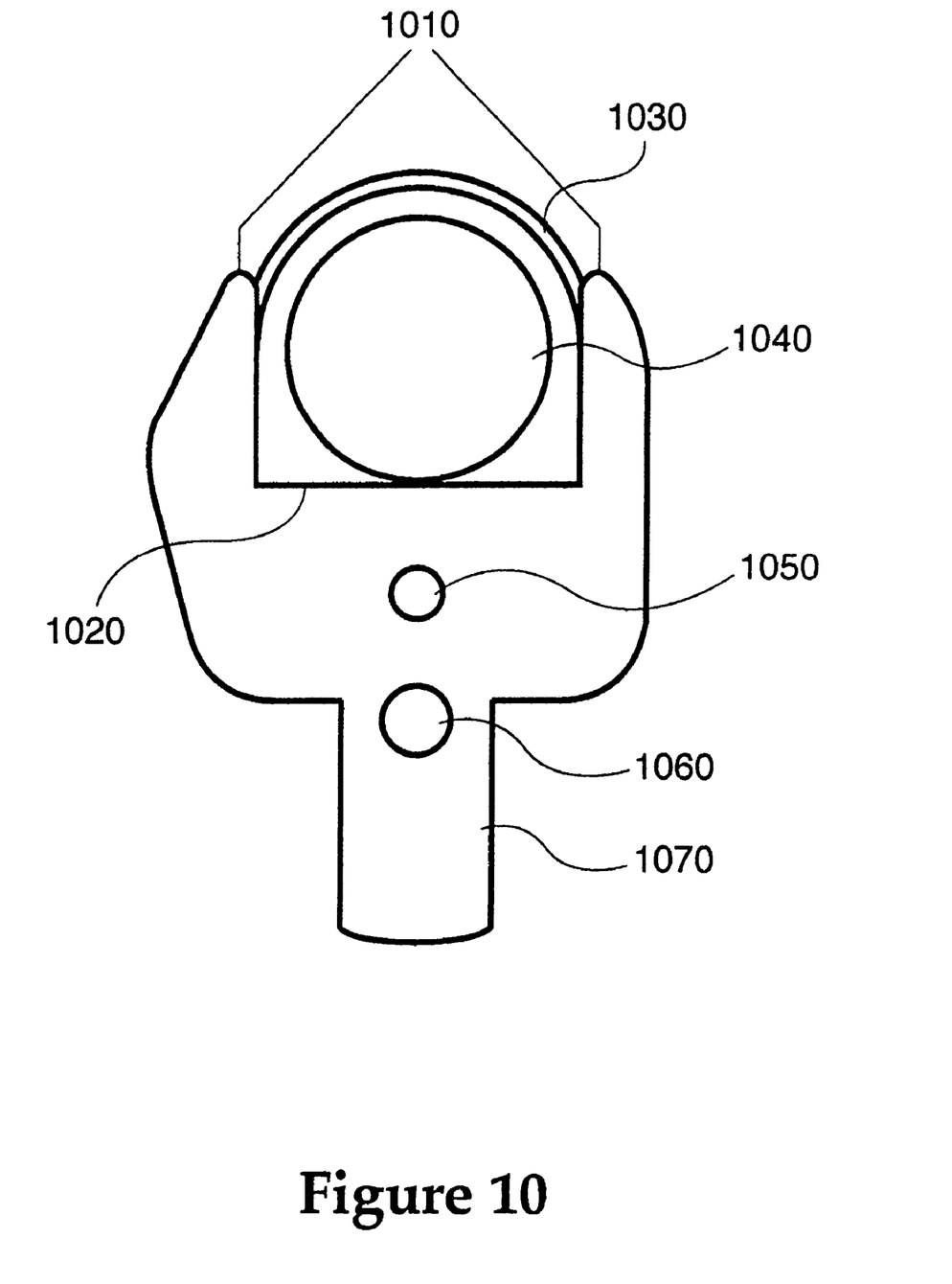
FIG. 10 illustrates a gigli saw cutting device to cut the humeral head.

To facilitate the installation of the humeral head component, the present invention also includes a device to cut the humeral head at its insertion with the rotator cuff along the anatomical neck. This device is illustrated in FIG. 10. This device has two small metallic guides 1010 that are placed on the cuff insertion posteriorly. The distance between the guides may be adjusted by turning knob 1050.

Anteriorly, a guide is used at the anterior capsular insertion point. The device includes a thin gigli saw, which is housed inside. The gigli saw is rotated, and thus severs the humeral head, by rotation of knob 1060. The device is slid up the humerus as the bone is cut, and the gigli saw ultimately resects the humeral head at the anatomical neck.

All patients should be evaluated before surgery. This evaluation comprises a thorough history and physical examination, including past history and allergies. The physical examination further comprises an examination of the shoulder and other body systems to evaluate a patient's fitness for surgery.

A complete clinical evaluation of the shoulder should be performed before surgery. On physical examination, special attention should be directed toward the patient's range of motion, including internal rotation contractures. Occurrence and type of pain reported by the patient, including pain at night, mechanical symptoms, and difficulties with daily activities, are important to note.

In addition to a physical examination, X-ray and computerized axial tomography ("CT") scans may be helpful. An X-ray evaluation should comprise at least an anteroposterior ("AP") projection of the shoulder and an axillary view. A CT scan of the shoulder may be helpful to evaluate the bony structure of the shoulder.

When reviewing CT scans or X-rays, it is important to note any wearing of the glenoid. It may be necessary to compensate for this wear, which changes the glenoid version, when reaming the glenoid for insertion of the artificial glenoid component. In addition, factors such as bone loss associated with previous surgeries or from chronic dislocations should be noted so that reconstruction can be appropriately planned.

A magnetic resonance image ("MRI") may also be helpful in evaluating the condition of the rotator cuff tendons. Rotator cuff condition should be noted prior to performing the operation so that problems, such as large tears, may be planned for in advance. In addition, total shoulder arthroplasty performed on patients with large rotator cuff tears are not typically as successful as hemi-arthroplasty in the same patient population.

The patient is usually placed in the beach chair position after induction of general anesthesia. The patient should be carefully positioned to allow complete access to the arm. The patient's shoulder should be off the table so that hyperextension is possible, thus facilitating shoulder dislocation and humeral head resection. The arm may be prepared using a standard technique. A patient's neck and head should be in a neutral position, and an arm holder may be useful to reduce the number of assistants required.

After preparation, a standard deltopectoral incision is made. The cephalic vein is isolated and mobilized medially or laterally depending on where it lies. The clavipectoral fascia is then opened just medial to the conjoined tendon, exposing the subscapularis muscle and tendon. The subscapularis tendon is then divided one centimeter medial to the lesser tuberosity. If an internal rotation contracture is present, lengthening can be performed.

The subscapularis tendon is now separated from the underlying capsule. The shoulder capsule can then be resected or released from its insertion on the glenoid labrum. Care must be taken to avoid injury to the axillary nerve which can be palpated just inferior to the axillary pouch. The remainder of the capsule is resected to completely free the glenohumeral joint.

Once freed, the glenohumeral joint should be inspected. The decision whether to perform a total shoulder or a hemi-arthroplasty can be confirmed at this time. At this point, the humeral head may be dislocated to allow better exposure, thus making resection of the humeral head easier.

To resect the humeral head, a special device is fashioned as shown in FIG. 10. The posterior portion of the device that contains a gigli saw is passed behind the humeral head and placed on the insertion of the rotator cuff tendons. The gigli saw is then advanced which resects the humeral head five millimeters proximal to the cuff insertion all the way around the head. An intramedullary reamer can then be passed into the humerus. The reamer may be used as a guide to the central axis of the humerus and does not need to be so large that all the cancelous bone is removed. The amount of anteversion and tilt can then be determined using intramedullary guides.

Once anteversion and tilt are determined, a rasp may be inserted into the reamed area. This is usually a 5-mm broach with a collar attached to protect the humeral metaphysis during preparation of the glenoid.

A forty-five degree drill guide with an appropriately sized drill bit is used to open up a central hole in the glenoid. Reamers may be used to remove remaining cartilage and to reorient the glenoid if needed. Glenoid version should have been determined preoperatively using either a CT scan or an axillary x-ray. Although other artificial glenoid designs may be used, a pegged artificial glenoid is preferred as it seems to be the most stable.

If substantial bone loss is present, it may be necessary to use a piece of the humeral head as structural autograft. Using part of the humeral head as a structural autograft may allow solid fixation of the artifical glenoid. Trial components can be used to insure proper fit. Once the proper component size is found, it should be left in place as a trial, until the entire joint can be reassembled and tested.

Once a trial artificial glenoid is in place, consecutive reamers can be used to open up the metaphysis, and remaining humeral osteophytes can be resected. The trial humeral head components are then inserted. The amount of offset is determined and the trial components are put into position in the joint and the joint is reassembled for testing.

The arm is taken into a full range of motion and the stability of the shoulder is assessed. Once the appropriate components are found, the artificial glenoid can be cemented into position, and the humeral component is press-fit into position. Some allograft cancelous bone may be used to maximize the amount of contact between the prosthetic humeral head component and the metaphysis.

In an alternative embodiment, the humeral component can be cemented into position using a mixture of calcium carbonate and bone morphogenic protein. This combination allows solid initial fixation as well as allowing in-growth of bone into the humeral component.

Once the artificial glenoid and humeral head have been properly replaced and the shoulder is in place, the wound can be closed using a non-absorbable suture to reattach the subscapularis tendon to its insertion on the lesser tuberosity. The deltopectoral groove is closed using an absorbable suture. Skin and subcutaneous tissues are closed in the usual manner. A dry sterile dressing is applied to the wound. A drain is used at the physician's discretion. FIG. 7 shows a diagram of the AP radiograph after insertion of the prosthesis. In an axillary view, the prosthesis appears as shown in FIG. 6.

In the event a fracture system is required, the implantation technique is similar to the previously described arthritic component implantation method. The deltopectoral approach is used to expose the fracture site. The fractured tuberosities are split and the humeral head removed. This may require cutting the head at the anatomical neck in a three-part fracture. The prosthesis is then impacted into the remaining metaphysis or shaft of the humerus. The shaft or metaphysis may require broaching to insure the best fit of the component in the distal fragment. A trial component is then placed into position so that the soft tissue balance can be assessed.

The component is usually left proud so that the when the fractured tuberosities are sewn to the metaphyseal portion and the cuff will continue to function correctly. The tuberosities are repaired by passing three-millimeter Dacron tape through the rotator cuff at its insertion on the tuberosities. The tape is then crossed and passed through the bone of the tuberosities. One suture limb is then passed through the fin posteriorly and tied to the limb of the lesser tuberosity. One limb of the suture from the lesser tuberosity fragment is then passed medially through the fin and tied with a limb from the greater tuberosity. This should fix the tuberosities solidly to stem.

Cement may be required to fix the stem to the shaft of the humerus. If a good press fit can be obtained, cement may not be required. Care should be taken to make sure the component is solidly fixed at the proper height.

Post-operatively the patient should be started on passive range of motion exercises the day following surgery. However, it is important to protect the subscapularis at this point so as not to impact its repair. External rotation is usually limited to ten degrees for approximately six weeks. During this time, a sling or immobilizer may be worn for comfort.

Active, assisted exercises may be added after four weeks, and strengthening exercises can be added typically eight to ten weeks after surgery, depending on patient progress. X-rays (AP and Axillary) are performed at six weeks, six months, and one year after the surgery. After the first year, annual radiographs, as well as a clinical evaluation, should be performed.

While the invention has been particularly shown and described with reference to a preferred embodiment thereof, it will be understood by those skilled in the art that various changes in form and details may be made therein without departing from the spirit and scope of the invention.

The embodiments of the invention in which an exclusive property or privilege is claimed are defined as follows:

1. A shoulder prosthesis comprising:
    an implant has a metaphseal body sized to fit into the metaphysis of the humerus such that the metaphysis requires only a minimal amount of reaming for receipt of said metaphseal body;
    a modular humeral head mounting means fixedly attached to a side of said metaphyseal body;
    a stem attached to and extending from a bottom portion of said metaphyseal body; substantially opposite said modular head mounting means, said stem being shorter than said metaphyseal body and configured to extend no more than two centimeters into the diaphysis of the humerus;
    a modular artificial humeral head of a size and shape selected to approximate the natural humeral head which it replaces, said head being attachable to said implant; and
    said modular head mounting means being of a size selected to fit into the metaphysis of the humerus such that said metaphyseal body comprised of a material that allows for bone ingrowth.

2. The shoulder prosthesis of claim 1, also including a glenoid component, wherein said glenoid component has height, width, and curvature selected to approximate the natural glenoid it replaces.

3. A tool for removing the humeral head comprising:
    a rear guide;
    an anterior guide and handle fixedly attached to said rear guide;
    two lateral guides movably affixed to said rear guide;
    a lateral guide spacing control means located on either of said rear and anterior guides for altering spacing between said lateral guides;
    a flexible saw blade, wherein said flexibility, in conjunction with the spacing between said lateral guides, allows said saw blade to approximate the shape of the humerus; and,
    a mechanical saw blade activation means located on said rear guide.

4. A prosthesis implantation and fixation method, comprising the steps of:
    resecting the humeral head;
    selecting a metaphyseal implant that is of a size which allows implantation of said metaphyseal implant with a minimum of metaphyseal reaming, where said metaphyseal implant has a distal portion that does not extend more than two centimeters into the diaphysis
    reaming only enough of the metaphysis to allow said implant to be press fit therein;
    inserting said metaphyseal implant into the metaphysis;
    selecting a modular humeral head, wherein said modular head is of a size and shape substantially equal to the resected humeral head; and,
    attaching said humeral head to said implant.

5. The prosthesis implantation method of claim 4, further comprising the steps:
    removing the natural glenoid;
    selecting an artificial glenoid, wherein said artificial glenoid is of a height, width, and curvature substantially similar to the natural glenoid it replaces; and,
    attaching said artificial glenoid in place of said natural glenoid.

6. The prosthesis implant method of claim 4, wherein the homeral head having a metaphyseal surface comprised of a material that allows for bone growth.

7. The prosthesis implant method of claim 4, further comprising the step of placing a collar has a metaphyseal between said modular humeral head and said implant, wherein the metaphyseal surface of said collar comprised of a material that allows for bone ingrowth.

* * * * *